United States Patent
Bontus et al.

(10) Patent No.: US 9,439,579 B2
(45) Date of Patent: Sep. 13, 2016

(54) APPARATUS AND METHOD FOR INFLUENCING AND/OR DETECTING MAGNETIC PARTICLES

(75) Inventors: Claas Bontus, Hamburg (DE); Bernhard Gleich, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 434 days.

(21) Appl. No.: 13/989,431

(22) PCT Filed: Dec. 5, 2011

(86) PCT No.: PCT/IB2011/055456
§ 371 (c)(1),
(2), (4) Date: May 24, 2013

(87) PCT Pub. No.: WO2012/077035
PCT Pub. Date: Jun. 14, 2012

(65) Prior Publication Data
US 2013/0253304 A1    Sep. 26, 2013

(30) Foreign Application Priority Data

Dec. 10, 2010 (EP) .................................. 10194503

(51) Int. Cl.
*A61B 5/05* (2006.01)
(52) U.S. Cl.
CPC .................................. *A61B 5/0515* (2013.01)
(58) Field of Classification Search
CPC .................................................. A61B 5/0515
See application file for complete search history.

(56) References Cited

U.S. PATENT DOCUMENTS

| 5,105,167 A | 4/1992 | Peczalski |
| 2005/0242877 A1 | 11/2005 | Kusunoki et al. |
| 2006/0211939 A1* | 9/2006 | Gleich ..................... A61B 5/05 600/410 |
| 2008/0204009 A1 | 8/2008 | Gleich et al. |

(Continued)

FOREIGN PATENT DOCUMENTS

| DE | 10151778 | 5/2003 |
| EP | 1304542 | 4/2003 |

(Continued)

OTHER PUBLICATIONS

B. Gleich et al., "Tomographic Imaging Using the Nonlinear Response of Magnetic Particles", Nature, vol. 435, pp. 1214-1217.

*Primary Examiner* — Ruth S Smith

(57) ABSTRACT

Method for influencing and/or detecting magnetic particles in a field of view. Selection coils/magnets generate a magnetic selection field and drive coils generate a magnetic drive field for moving a field-free point along a predetermined trajectory through the field of view, changing the magnetization of the magnetic material locally. The drive field comprises a time-dependent oscillating drive field current per drive field coil having one or more individual oscillating frequencies and one or more individual current amplitudes and being generated by a corresponding drive field voltage generated by a superposition of a number of drive field voltage components including a drive field voltage component per drive field coil, wherein a drive field voltage component corresponding to a drive field coil comprises one or more sub-components, each having an individual voltage amplitude and having the same individual oscillating frequency as the respective drive field current of said particular drive field coil.

13 Claims, 5 Drawing Sheets

(56) References Cited

U.S. PATENT DOCUMENTS

| | | |
|---|---|---|
| 2008/0309330 A1 | 12/2008 | Ohyu et al. |
| 2009/0115415 A1 | 5/2009 | Weaver et al. |
| 2009/0201089 A1 | 8/2009 | Kawanabe et al. |

FOREIGN PATENT DOCUMENTS

| | | |
|---|---|---|
| WO | WO2004091386 | 10/2004 |
| WO | WO2004091390 | 10/2004 |
| WO | WO2004091394 | 10/2004 |
| WO | WO2004091395 | 10/2004 |
| WO | WO2004091396 | 10/2004 |
| WO | WO2004091397 | 10/2004 |
| WO | WO2004091398 | 10/2004 |
| WO | WO2004091408 | 10/2004 |
| WO | WO2010008478 | 1/2010 |

* cited by examiner

APPARATUS AND METHOD FOR INFLUENCING AND/OR DETECTING MAGNETIC PARTICLES

FIELD OF THE INVENTION

The present invention relates to an apparatus and a method for influencing and/or detecting magnetic particles in a field of view. Further, the present invention relates to a computer program for implementing said method on a computer and for controlling such an apparatus. The present invention relates particularly to the field of Magnetic Particle Imaging.

BACKGROUND OF THE INVENTION

Magnetic Particle Imaging (MPI) is an emerging medical imaging modality. The first versions of MPI were two-dimensional in that they produced two-dimensional images. Newer versions are three-dimensional (3D). A four-dimensional image of a non-static object can be created by combining a temporal sequence of 3D images to a movie, provided the object does not significantly change during the data acquisition for a single 3D image.

MPI is a reconstructive imaging method, like Computed Tomography (CT) or Magnetic Resonance Imaging (MRI). Accordingly, an MP image of an object's volume of interest is generated in two steps. The first step, referred to as data acquisition, is performed using an MPI scanner. The MPI scanner has means to generate a static magnetic gradient field, called the "selection field", which has a (single) field-free point (FFP) at the isocenter of the scanner. Moreover, this FFP is surrounded by a first sub-zone with a low magnetic field strength, which is in turn surrounded by a second sub-zone with a higher magnetic field strength. In addition, the scanner has means to generate a time-dependent, spatially nearly homogeneous magnetic field. Actually, this field is obtained by superposing a rapidly changing field with a small amplitude, called the "drive field", and a slowly varying field with a large amplitude, called the "focus field". By adding the time-dependent drive and focus fields to the static selection field, the FFP may be moved along a predetermined FFP trajectory throughout a "volume of scanning" surrounding the isocenter. The scanner also has an arrangement of one or more, e.g. three, receive coils and can record any voltages induced in these coils. For the data acquisition, the object to be imaged is placed in the scanner such that the object's volume of interest is enclosed by the scanner's field of view, which is a subset of the volume of scanning.

The object must contain magnetic nanoparticles; if the object is an animal or a patient, a contrast agent containing such particles is administered to the animal or patient prior to the scan. During the data acquisition, the MPI scanner moves the FFP along a deliberately chosen trajectory that traces out/covers the volume of scanning, or at least the field of view. The magnetic nanoparticles within the object experience a changing magnetic field and respond by changing their magnetization. The changing magnetization of the nanoparticles induces a time-dependent voltage in each of the receive coils. This voltage is sampled in a receiver associated with the receive coil. The samples output by the receivers are recorded and constitute the acquired data. The parameters that control the details of the data acquisition make up the "scan protocol".

In the second step of the image generation, referred to as image reconstruction, the image is computed, or reconstructed, from the data acquired in the first step. The image is a discrete 3D array of data that represents a sampled approximation to the position-dependent concentration of the magnetic nanoparticles in the field of view. The reconstruction is generally performed by a computer, which executes a suitable computer program. Computer and computer program realize a reconstruction algorithm. The reconstruction algorithm is based on a mathematical model of the data acquisition. As with all reconstructive imaging methods, this model can be formulated as an integral operator that acts on the acquired data; the reconstruction algorithm tries to undo, to the extent possible, the action of the model.

Such an MPI apparatus and method have the advantage that they can be used to examine arbitrary examination objects—e.g. human bodies—in a non-destructive manner and with a high spatial resolution, both close to the surface and remote from the surface of the examination object. Such an apparatus and method are generally known and have been first described in DE 101 51 778 A1 and in Gleich, B. and Weizenecker, J. (2005), "Tomographic imaging using the nonlinear response of magnetic particles" in Nature, vol. 435, pp. 1214-1217, in which also the reconstruction principle is generally described. The apparatus and method for magnetic particle imaging (MPI) described in that publication take advantage of the non-linear magnetization curve of small magnetic particles.

Generally, in an MPI apparatus the magnetic gradient field (i.e. the magnetic selection field) is generated with a spatial distribution of the magnetic field strength such that the field of view comprises a first sub-area with lower magnetic field strength (e.g. the FFP), the lower magnetic field strength being adapted such that the magnetization of the magnetic particles located in the first sub-area is not saturated, and a second sub-area with a higher magnetic field strength, the higher magnetic field strength being adapted such that the magnetization of the magnetic particles located in the second sub-area is saturated. Due to the non-linearity of the magnetization characteristic curve of the magnetic particles the magnetization and thereby the magnetic field generated by the magnetic particles shows higher harmonics, which, for example, can be detected by a detection coil. The evaluated signals (the higher harmonics of the signals) contain information about the spatial distribution of the magnetic particles, which again can be used e.g. for medical imaging, for the visualization of the spatial distribution of the magnetic particles and/or for other applications.

Thus, the MPI apparatus and the MPI method are generally based on a new physical principle (i.e. the principle referred to as MPI) that is different from other known conventional medical imaging techniques, as for example local magnetic resonance (LMR) or nuclear magnetic resonance (NMR). In particular, this new MPI-principle, does, in contrast to LMR and NMR, not exploit the influence of the material on the magnetic resonance characteristics of protons, but rather directly detects the magnetization of the magnetic material by exploiting the non-linearity of the magnetization characteristic curve. In particular, the MPI-technique exploits the higher harmonics of the generated magnetic signals which result from the non-linearity of the magnetization characteristic curve in the area where the magnetization changes from the non-saturated to the saturated state.

As explained above in an MPI apparatus multiple coils are used to generate and manipulate a desired well-defined magnetic field. Consequently, control signals are used to drive said various coils. However, various coils couple so that the control signal applied to a channel needs to compensate for the coupling between coils. This results in the control signal applied to a channel to display beats when the signal is plotted as a function of time, which beats may differ in the maximum amplitude.

Before being applied to a channel, a control signal is generally amplified by an amplifier. However, the amplifier may not be able to handle the maximum amplitude present in the beating control signal. If the maximum amplitude present in the control signal exceeds the upper limit of the amplifier, a channel does not receive the required control signal resulting in less than optimal results in magnetic field.

SUMMARY OF THE INVENTION

It is an object of the present invention to provide an apparatus and a method for influencing and/or detecting magnetic particles in a field of view to enable amplification of control signals regardless of whether or not the maximum amplitudes in the control signals exceed the upper limit of an amplifier that is used to amplify the control signals.

In a first aspect of the present invention an apparatus is presented comprising:

selection means comprising a selection field signal generator unit and selection field elements for generating a magnetic selection field having a pattern in space of its magnetic field strength such that a first sub-zone having a low magnetic field strength where the magnetization of the magnetic particles is not saturated and a second sub-zone having a higher magnetic field strength where the magnetization of the magnetic particles is saturated are formed in the field of view, drive means comprising a drive field signal generator unit and drive field coils for changing the position in space of the two sub-zones in the field of view by means of a magnetic drive field so that the magnetization of the magnetic material changes locally, wherein said drive field signal generator unit is adapted to provide a time-dependent oscillating drive field current per drive field coil for driving the respective drive field coil, each drive field current having one or more individual oscillating frequencies and one or more individual current amplitudes and being generated by a corresponding drive field voltage per drive field coil, each drive field voltage being generated by a superposition of a number of drive field voltage components including a drive field voltage component per drive field coil, wherein a drive field voltage component corresponding to a particular drive field coil comprises one or more sub-components, a sub-component having an individual voltage amplitude and having the same individual oscillating frequency as the respective drive field current of said particular drive field coil.

In a further aspect of the present invention a corresponding method is presented.

In still a further aspect of the present invention a corresponding drive field signal generator unit for use in an apparatus as defined above is presented.

Preferred embodiments of the invention are defined in the dependent claims. It shall be understood that the claimed method, the claimed drive field signal generator unit and the claimed computer program have similar and/or identical preferred embodiments as the claimed apparatus and as defined in the dependent claims.

The present invention is based on the idea to control the output of the drive field generator units, in particular of an amplifier generally included in each drive field generator unit, such that drive field voltages are generated for driving the drive field coils such that the desired drive field currents are running through the drive field coils by which the field-free point, i.e. the first sub-zone, move along the desired path (trajectory), e.g. a Lissajous trajectory. The number of individual oscillating frequencies and individual current amplitudes of the drive field currents depends on the desired trajectory.

For instance, for a Lissajous trajectory each drive field current comprises a single oscillating frequency and one or two current amplitudes (e.g. two amplitudes if the drive field current comprises a sin-term and a cos-term, both with the same oscillating frequency). Accordingly, for each drive coil a corresponding drive field voltage is generated as a superposition of a number of drive field voltage components. Thus, in case of three drive field coils a drive field voltage comprises three drive field voltage components. Each drive field voltage component corresponding to a particular drive field coil comprises one or more sub-component. Each sub-component has an individual voltage amplitude and an individual oscillating frequency, wherein said individual oscillating frequency corresponds to the oscillating frequency of the respective drive field current of said particular drive field coil. In other words, for the different oscillating frequencies of the different drive field currents corresponding voltage sub-components having a corresponding oscillating frequency are provided in a drive field voltage.

Preferably, the drive field signal generator unit is adapted to generate said drive field voltages such that each drive field voltage component comprises a first sub-component having the form of a cosine function and a cosine voltage amplitude and a second sub-component having the form of a sine function and a sine voltage amplitude, wherein both sub-components have the same oscillating frequency. For instance, in a practical and simple embodiment each drive field voltage generally has the form of:

$$U_m(t) = U_{mx01} \cos(\omega_x t) + U_{mx02} \sin(\omega_x t) + U_{my01} \cos(\omega_y t) + U_{my02} \sin(\omega_y t) + U_{mz01} \cos(\omega_z t) + U_{mz02} \sin(\omega_z t)$$

wherein m=x, y, z depending on the respective drive field coil, $\omega$ is the respective oscillating frequency and $U_{mn01}$ and $U_{mn02}$, n=x, y, z, are the respective voltage amplitudes.

In this embodiment each drive field voltage $U_m(t)$ comprises three components (one for each of the three different oscillating frequencies $\omega_x$, $\omega_y$, $\omega_z$ of the three different drive field currents of the three different drive field coils), e.g. the component for the oscillating frequency $\omega_x$ being $U_{mx01} \cos(\omega_x t) + U_{mx02} \sin(\omega_x t)$, and each of said three components comprises two sub-components, e.g. for the oscillating frequency $\omega_x$ being $U_{mx01} \cos(\omega_x t)$ and $U_{mx02} \sin(\omega_x t)$. It shall, however, be noted that, if there are more or less drive field coils, e.g. for more, less or different directions than the direction x, y, z, each drive field voltage generally also comprises more or less components with respective oscillating frequencies.

By this embodiment a desired trajectory for the movement of the field-free point (i.e. the first sub-zone), e.g. a Lissajous trajectory, can be easily realized. In other embodiments, e.g. for realizing other trajectories as mentioned above, more sub-components (having an individual oscillating frequency and voltage amplitude) are added together into each drive field voltage component. It should further be noted that in the above equations more components can be added if more that three drive field coils are used.

In an embodiment it is proposed that said drive field signal generator unit is adapted to generate said drive field voltages such that at least one, in particular each, drive field voltage component comprises a superposition of two or more sub-components, wherein the first sub-component has a frequency corresponding to the oscillating frequency of the respective drive field current of said particular drive field coil and at least one, in particular each, further sub-component has a frequency corresponding to a different multiple of said oscillating frequency of said respective drive field current. In this embodiment the invention proposes to add higher harmonics to the control signal to be amplified. The higher harmonics, preferably integer multiples, are added such that the maximum amplitude of the control signal that is fed to the amplifier does not exceed the upper limit of the amplifier. After amplification, a filter is preferably used to filter out the amplified higher harmonics. The resultant signal looks as if the amplifier has amplified the original control signal (with the maximum amplitude exceeding the upper limit of the amplifier). The invention thus enables amplification of signals exceeding the upper limit of the amplifier that is used for amplification.

According to a preferred embodiment said further sub-components have a frequency corresponding to an increasing odd multiple of said oscillating frequency of said respective drive field current. In an embodiment said sub-components are combinations of sin- and cos-terms which shall be replaced by other functions of the same periodicity. Sine functions are even, and cosine functions are odd. Replacing them by other functions of the same periodicity and also being even and odd, respectively, a Fourier analysis results in functions having only odd multiples of the same oscillating frequency (i.e. odd harmonics). However, it should be noted that other embodiments, i.e. embodiments using also (or only) even harmonics are possible as well.

Each drive field voltage component advantageously comprises a superposition of two to ten sub-components, in particular of three to five sub-components. Adding higher sub-components generally does not have significant effects since the used amplifiers have an upper frequency limit.

In a preferred exemplary implementation each drive field voltage $\tilde{U}_m(t)$ generally has the form of:

$$\tilde{U}_m(t) = \tilde{U}_{mx}(t) + \tilde{U}_{my}(t) + \tilde{U}_{mz}(t),$$

wherein each component $\tilde{U}_{mn}(t)$ has the form of $$\tilde{U}_{mn}(t) = \begin{cases} \frac{U_{mn02}}{\cos \alpha}(\sin(\beta) + \lambda_{s3}\ \sin(3\beta) + \lambda_{s5}\ \sin(5\beta) + \lambda_{s7}\ \sin(7\beta)), & \text{if } |U_{mn02}| > |U_{mn01}| \\ \frac{U_{mn01}}{\cos \alpha}(\cos(\beta) + \lambda_{c3}\ \cos(3\beta) + \lambda_{c5}\ \cos(5\beta) + \lambda_{c7}\ \cos(7\beta)) & \text{else.} \end{cases}$$

wherein $$\alpha = \begin{cases} \mathrm{atan2}(U_{mn01}, U_{mn02}), & \text{if } |U_{mn02}| > |U_{mn01}| \\ \mathrm{atan2}(U_{mn02}, U_{mn01}), & \text{else,} \end{cases}$$

$$\beta = \begin{cases} \omega_n t + \alpha, & \text{if } |U_{mn02}| > |U_{mn01}| \\ \omega_n t - \alpha, & \text{else,} \end{cases}$$

$$\lambda_{c3} = -\frac{2\ \sin^2\!\left(\frac{\pi}{2}\kappa\right)\ \sin(\pi\kappa)}{3(\pi(1-\kappa)+\sin(\pi\kappa))},\ \lambda_{c5} = \frac{-3\ \sin(2\pi\kappa) + 2\ \sin(3\pi\kappa)}{30(\pi(1-\kappa)+\sin(\pi\kappa))},\ \lambda_{c7} = \frac{-4\ \sin(3\pi\kappa) + 3\ \sin(4\pi\kappa)}{84(\pi(1-\kappa)+\sin(\pi\kappa))},$$

and $$\lambda_{s3} = \frac{2\ \sin^2\!\left(\frac{\pi}{2}\kappa\right)\ \sin(\pi\kappa)}{3(\pi(1-\kappa)+\sin(\pi\kappa))},\ \lambda_{s5} = \frac{-3\ \sin(2\pi\kappa) + 2\ \sin(3\pi\kappa)}{30(\pi(1-\kappa)+\sin(\pi\kappa))},\ \lambda_{s7} = \frac{4\ \sin(3\pi\kappa) - 3\ \sin(4\pi\kappa)}{84(\pi(1-\kappa)+\sin(\pi\kappa))},$$

wherein $\kappa$ is a so-called correction parameter.

In this embodiment each drive field voltage component $\tilde{U}_{mn}(t)$ comprises four sub-components, one sub-component for the base frequency (here called $\omega_n$ and included in the parameter $\beta$) and three further sub-components for higher harmonics of the same base frequency. As mentioned above, the number of components (here: three) may be different, dependent on the number of drive field coil, and also the number of sub-components (here: four) in each component may be different from four and may also be different in each component although it is preferably equal in each component.

In this implementation said correction parameter $\kappa$ has a value in the range from 0 to 1, in particular in the range from 0.3 to 0.7, which correction parameter $\kappa$ preferably has an identical predetermined value for all sub-components or different values for different sub-components and/or different terms of said sub-components.

In an embodiment the drive field signal generator unit further comprises a drive field generator control unit for controlling the generation of said drive field voltages such that one or more, in particular all, further sub-components having a frequency corresponding to a different multiple of said oscillating frequency of said respective drive field current are switchably added to the first sub-component only at predetermined time periods and/or under predetermined conditions, in particular if the amplitude of the drive field voltage exceeds a predetermined drive field voltage threshold. Thus, only when needed, such sub-components are generally added to the base frequency sub-component.

Preferably, said drive field generator control unit is adapted for switching the addition of one or more further sub-components at time points at which the respective sub-component has a function value of substantially zero to avoid additional disturbing effects on the desired drive field currents, e.g. incorrect components being added.

With the apparatus according to the present invention various applications are enabled. For instance, instruments or a probe of medicine provided with magnetic particles can be manipulated (moved) by use of the magnetic fields. Further, imaging can be performed. For this purpose the apparatus further comprises receiving means comprising at least one signal receiving unit and at least one receiving coil for acquiring detection signals, which detection signals depend on the magnetization in the field of view, which magnetization is influenced by the change in the position in space of the first and second sub-zone.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Before the details of the present invention shall be explained, basics of magnetic particle imaging shall be explained in detail with reference to FIGS. 1 to 4. In particular, two embodiments of an MPI scanner for medical diagnostics will be described. An informal description of the data acquisition will also be given. The similarities and differences between the two embodiments will be pointed out.

Figure 1:
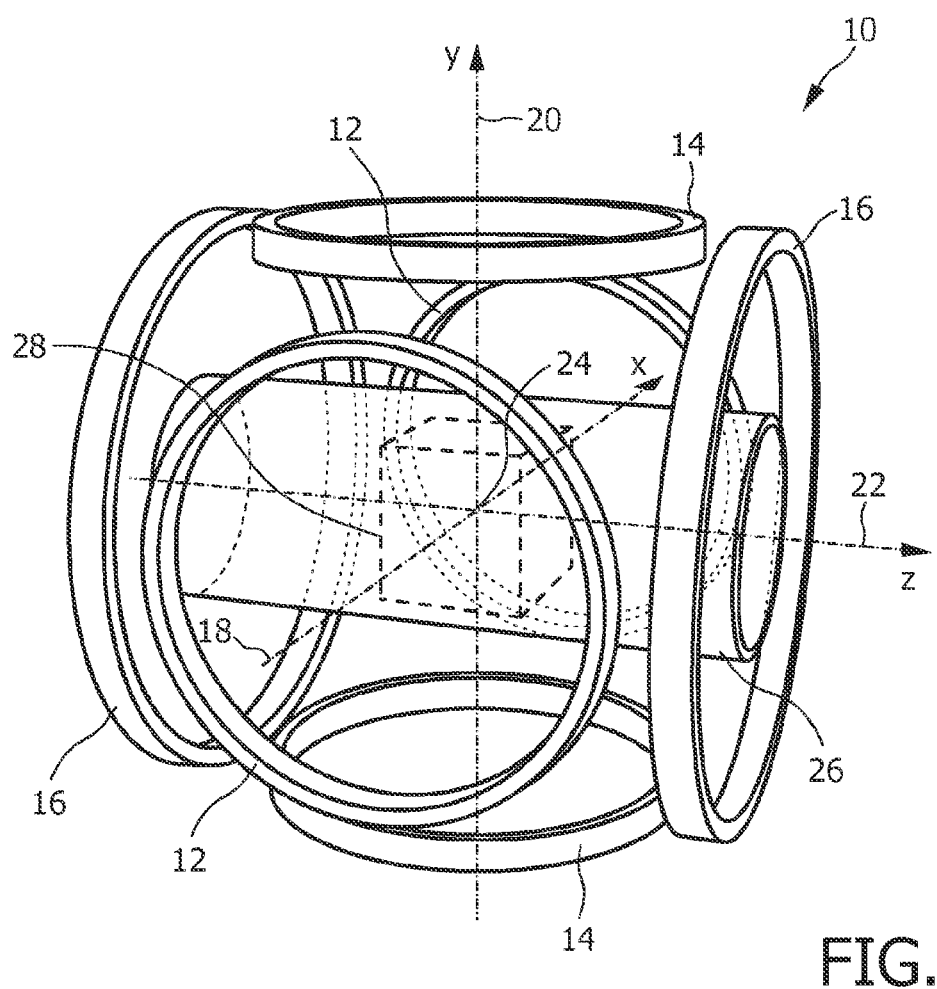
FIG. 1 shows a first embodiment of an MPI apparatus.

The first embodiment 10 of an MPI scanner shown in FIG. 1 has three pairs 12, 14, 16 of coaxial parallel circular coils, these coil pairs being arranged as illustrated in FIG. 1. These coil pairs 12, 14, 16 serve to generate the selection field as well as the drive and focus fields. The axes 18, 20, 22 of the three coil pairs 12, 14, 16 are mutually orthogonal and meet in a single point, designated the isocenter 24 of the MPI scanner 10. In addition, these axes 18, 20, 22 serve as the axes of a 3D Cartesian x-y-z coordinate system attached to the isocenter 24. The vertical axis 20 is nominated the y-axis, so that the x- and z-axes are horizontal. The coil pairs 12, 14, 16 are named after their axes. For example, the y-coil pair 14 is formed by the coils at the top and the bottom of the scanner. Moreover, the coil with the positive (negative) y-coordinate is called the y$^+$-coil (y$^-$-coil), and similarly for the remaining coils. When more convenient, the coordinate axes and the coils shall be labeled with $x_1$, $x_2$, and $x_3$, rather than with x, y, and z.

The scanner 10 can be set to direct a predetermined, time-dependent electric current through each of these coils 12, 14, 16, and in either direction. If the current flows clockwise around a coil when seen along this coil's axis, it will be taken as positive, otherwise as negative. To generate the static selection field, a constant positive current $I^S$ is made to flow through the z$^+$-coil, and the current $-I^S$ is made to flow through the z$^-$-coil. The z-coil pair 16 then acts as an anti-parallel circular coil pair.

It should be noted here that the arrangement of the axes and the nomenclature given to the axes in this embodiment is just an example and might also be different in other embodiments. For instance, in practical embodiments the vertical axis is often considered as the z-axis rather than the y-axis as in the present embodiment. This, however, does not generally change the function and operation of the device and the effect of the present invention.

Figure 2:
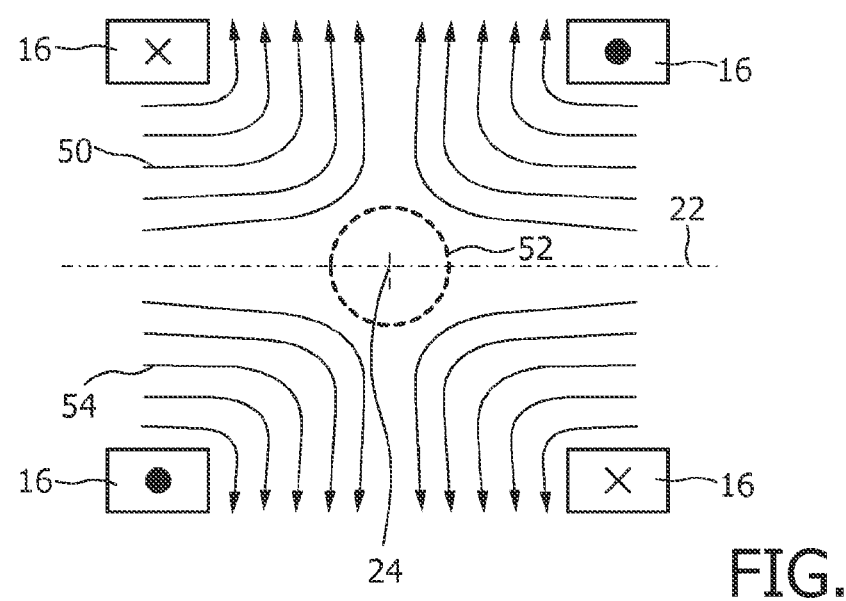
FIG. 2 shows an example of the selection field pattern produced by an apparatus as shown in FIG. 1.

The magnetic selection field, which is generally a magnetic gradient field, is represented in FIG. 2 by the field lines 50. It has a substantially constant gradient in the direction of the (e.g. horizontal) z-axis 22 of the z-coil pair 16 generating the selection field and reaches the value zero in the isocenter 24 on this axis 22. Starting from this field-free point (not individually shown in FIG. 2), the field strength of the magnetic selection field 50 increases in all three spatial directions as the distance increases from the field-free point. In a first sub-zone or region 52 which is denoted by a dashed line around the isocenter 24 the field strength is so small that the magnetization of particles present in that first sub-zone 52 is not saturated, whereas the magnetization of particles present in a second sub-zone 54 (outside the region 52) is in a state of saturation. In the second sub-zone 54 (i.e. in the residual part of the scanner's field of view 28 outside of the first sub-zone 52) the magnetic field strength of the selection field is sufficiently strong to keep the magnetic particles in a state of saturation.

By changing the position of the two sub-zones 52, 54 (including the field-free point) within the field of view 28 the (overall) magnetization in the field of view 28 changes. By determining the magnetization in the field of view 28 or physical parameters influenced by the magnetization, information about the spatial distribution of the magnetic particles in the field of view 28 can be obtained. In order to change the relative spatial position of the two sub-zones 52, 54 (including the field-free point) in the field of view 28, further magnetic fields, i.e. the magnetic drive field, and, if applicable, the magnetic focus field, are superposed to the selection field 50.

To generate the drive field, a time dependent current $I^D_1$ is made to flow through both x-coils 12, a time dependent current $I^D_2$ through both y-coils 14, and a time dependent current $I^D_3$ through both z-coils 16. Thus, each of the three coil pairs acts as a parallel circular coil pair. Similarly, to generate the focus field, a time dependent current $I^F_1$ is made to flow through both x-coils 12, a current $I^F_2$ through both y-coils 14, and a current $I^F_3$ through both z-coils 16.

It should be noted that the z-coil pair 16 is special: It generates not only its share of the drive and focus fields, but also the selection field (of course, in other embodiments, separate coils may be provided). The current flowing through the z$^\pm$-coil is $I^D_3+I^F_3\pm I^S$. The current flowing through the remaining two coil pairs 12, 14 is $I^D_k+I^F_k$, k=1, 2. Because of their geometry and symmetry, the three coil pairs 12, 14, 16 should be decoupled as good as possible, which in reality they are often not sufficiently enough.

Being generated by an anti-parallel circular coil pair, the selection field is rotationally symmetric about the z-axis, and its z-component is nearly linear in z and independent of x and y in a sizeable volume around the isocenter 24. In particular, the selection field has a single field-free point (FFP) at the isocenter. In contrast, the contributions to the drive and focus fields, which are generated by parallel circular coil pairs, are spatially nearly homogeneous in a sizeable volume around the isocenter 24 and parallel to the axis of the respective coil pair. The drive and focus fields jointly generated by all three parallel circular coil pairs are spatially nearly homogeneous and can be given any direction and strength, up to some maximum strength. The drive and focus fields are also time-dependent. The difference between the focus field and the drive field is that the focus field varies slowly in time and may have a large amplitude, while the drive field varies rapidly and has a small amplitude. There are physical and biomedical reasons to treat these fields differently. A rapidly varying field with a large amplitude would be difficult to generate and potentially hazardous to a patient.

In a practical embodiment the FFP can be considered as a mathematical point, at which the magnetic field is assumed to be zero. The magnetic field strength increases with increasing distance from the FFP, wherein the increase rate might be different for different directions (depending e.g. on the particular layout of the device). As long as the magnetic field strength is below the field strength required for bringing a magnetic particles into the state of saturation, the particle actively contributes to the signal generation of the signal measured by the device; otherwise, the particles is saturated and does not generate any signal.

The embodiment 10 of the MPI scanner has at least one further pair, preferably three further pairs, of parallel circular coils, again oriented along the x-, y-, and z-axes. These coil pairs, which are not shown in FIG. 1, serve as receive coils. As with the coil pairs 12, 14, 16 for the drive and focus fields, the magnetic field generated by a constant current flowing through one of these receive coil pairs is spatially nearly homogeneous within the field of view and parallel to the axis of the respective coil pair. The receive coils are supposed to be well decoupled. The time-dependent voltage induced in a receive coil is amplified and sampled by a receiver attached to this coil. More precisely, to cope with the enormous dynamic range of this signal, the receiver samples the difference between the received signal and a reference signal. The transfer function of the receiver is non-zero from zero Hertz ("DC") up to the frequency where the expected signal level drops below the noise level.

The embodiment 10 of the MPI scanner shown in FIG. 1 has a cylindrical bore 26 along the z-axis 22, i.e. along the axis of the selection field. All coils are placed outside this bore 26. For the data acquisition, the patient (or object) to be imaged is placed in the bore 26 such that the patient's volume of interest—that volume of the patient (or object) that shall be imaged—is enclosed by the scanner's field of view 28—that volume of the scanner whose contents the scanner can image. The patient (or object) is, for instance, placed on a patient table. The field of view 28 is a geometrically simple, isocentric volume in the interior of the bore 26, such as a cube, a ball, a cylinder or an arbitrary shape. A cubical field of view 28 is illustrated in FIG. 1.

The size of the first sub-zone 52 is dependent on the strength of the gradient of the magnetic selection field and on the field strength of the magnetic field required for saturation, which in turn depends on the magnetic particles. For a sufficient saturation of typical magnetic particles at a magnetic field strength of 80 A/m and a gradient (in a given space direction) of the field strength of the magnetic selection field amounting to $50 \times 10^3$ A/m$^2$, the first sub-zone 52 in which the magnetization of the particles is not saturated has dimensions of about 1 mm (in the given space direction).

The patient's volume of interest is supposed to contain magnetic nanoparticles. Prior to the diagnostic imaging of, for example, a tumor, the magnetic particles are brought to the volume of interest, e.g. by means of a liquid comprising the magnetic particles which is injected into the body of the patient (object) or otherwise administered, e.g. orally, to the patient.

Generally, various ways for bringing the magnetic particles into the field of view exist. In particular, in case of a patient into whose body the magnetic particles are to be introduced, the magnetic particles can be administered by use of surgical and non-surgical methods, and there are both methods which require an expert (like a medical practitioner) and methods which do not require an expert, e.g. can be carried out by laypersons or persons of ordinary skill or the patient himself/herself Among the surgical methods there are potentially non-risky and/or safe routine interventions, e.g. involving an invasive step like an injection of a contrast agent into a blood vessel (if such an injection is at all to be considered as a surgical method), i.e. interventions which do not require considerable professional medical expertise to be carried out and which do not involve serious health risks. Further, non-surgical methods like swallowing or inhalation can be applied.

Generally, the magnetic particles are pre-delivered or pre-administered before the actual steps of data acquisition are carried out. In embodiments, it is, however, also possible that further magnetic particles are delivered/administered into the field of view.

An embodiment of magnetic particles comprises, for example, a spherical substrate, for example, of glass which is provided with a soft-magnetic layer which has a thickness of, for example, 5 nm and consists, for example, of an iron-nickel alloy (for example, Permalloy). This layer may be covered, for example, by means of a coating layer which protects the particle against chemically and/or physically aggressive environments, e.g. acids. The magnetic field strength of the magnetic selection field 50 required for the saturation of the magnetization of such particles is dependent on various parameters, e.g. the diameter of the particles, the used magnetic material for the magnetic layer and other parameters.

In the case of e.g. a diameter of 10 μm with such magnetic particles, a magnetic field of approximately 800 A/m (corresponding approximately to a flux density of 1 mT) is then required, whereas in the case of a diameter of 100 μm a magnetic field of 80 A/m suffices. Even smaller values are obtained when a coating of a material having a lower saturation magnetization is chosen or when the thickness of the layer is reduced.

In practice, magnetic particles commercially available under the trade name Resovist (or similar magnetic particles) are often used, which have a core of magnetic material or are formed as a massive sphere and which have a diameter in the range of nanometers, e.g. 40 or 60 nm.

For further details of the generally usable magnetic particles and particle compositions, the corresponding parts of EP 1304542, WO 2004/091386, WO 2004/091390, WO 2004/091394, WO 2004/091395, WO 2004/091396, WO 2004/091397, WO 2004/091398, WO 2004/091408 are herewith referred to, which are herein incorporated by reference. In these documents more details of the MPI method in general can be found as well.

During the data acquisition, the x-, and z-coil pairs 12, 14, 16 generate a position- and time-dependent magnetic field, the applied field. This is achieved by directing suitable currents through the field generating coils. In effect, the drive and focus fields push the selection field around such that the FFP moves along a preselected FFP trajectory that traces out the volume of scanning—a superset of the field of view. The applied field orientates the magnetic nanoparticles in the patient. As the applied field changes, the resulting magnetization changes too, though it responds nonlinearly to the applied field. The sum of the changing applied field and the changing magnetization induces a time-dependent voltage $V_k$ across the terminals of the receive coil pair along the $x_k$-axis. The associated receiver converts this voltage to a signal $S_k$, which it processes further.

Figure 3:
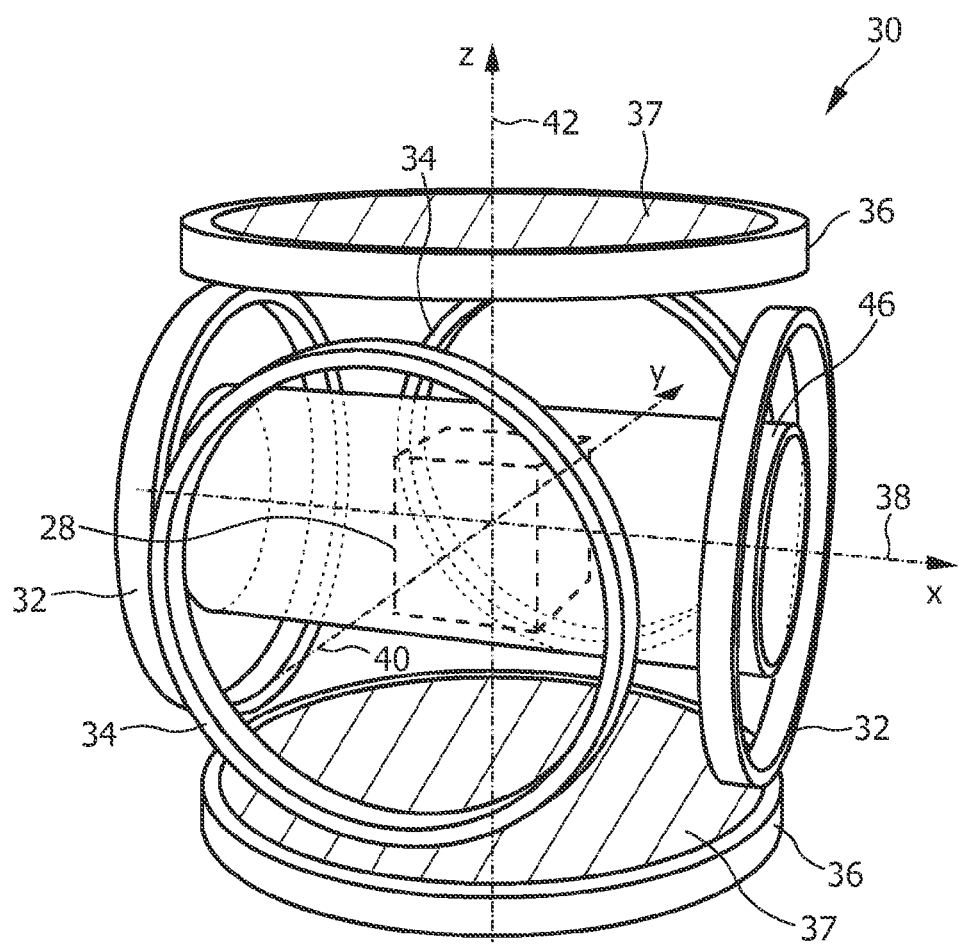
FIG. 3 shows a second embodiment of an MPI apparatus.

Like the first embodiment 10 shown in FIG. 1, the second embodiment 30 of the MPI scanner shown in FIG. 3 has three circular and mutually orthogonal coil pairs 32, 34, 36, but these coil pairs 32, 34, 36 generate the selection field and the focus field only. The z-coils 36, which again generate the selection field, are filled with ferromagnetic material 37. The z-axis 42 of this embodiment 30 is oriented vertically, while the x- and y-axes 38, 40 are oriented horizontally. The bore 46 of the scanner is parallel to the x-axis 38 and, thus, perpendicular to the axis 42 of the selection field. The drive field is generated by a solenoid (not shown) along the x-axis 38 and by pairs of saddle coils (not shown) along the two remaining axes 40, 42. These coils are wound around a tube which forms the bore. The drive field coils also serve as receive coils.

To give a few typical parameters of such an embodiment: The z-gradient of the selection field, G, has a strength of $G/\mu_0 = 2.5$ T/m, where $\mu_0$ is the vacuum permeability. The temporal frequency spectrum of the drive field is concentrated in a narrow band around 25 kHz (up to approximately 150 kHz). The useful frequency spectrum of the received signals lies between 50 kHz and 1 MHz (eventually up to approximately 15 MHz). The bore has a diameter of 120 mm. The biggest cube 28 that fits into the bore 46 has an edge length of $120 \text{ mm}/\sqrt{2} \approx 84$ mm.

Since the construction of field generating coils is generally known in the art, e.g. from the field of magnetic resonance imaging, this subject need not be further elaborated herein.

In an alternative embodiment for the generation of the selection field, permanent magnets (not shown) can be used. In the space between two poles of such (opposing) permanent magnets (not shown) there is formed a magnetic field which is similar to that shown in FIG. 2, that is, when the opposing poles have the same polarity. In another alternative embodiment, the selection field can be generated by a mixture of at least one permanent magnet and at least one coil.

Figure 4:
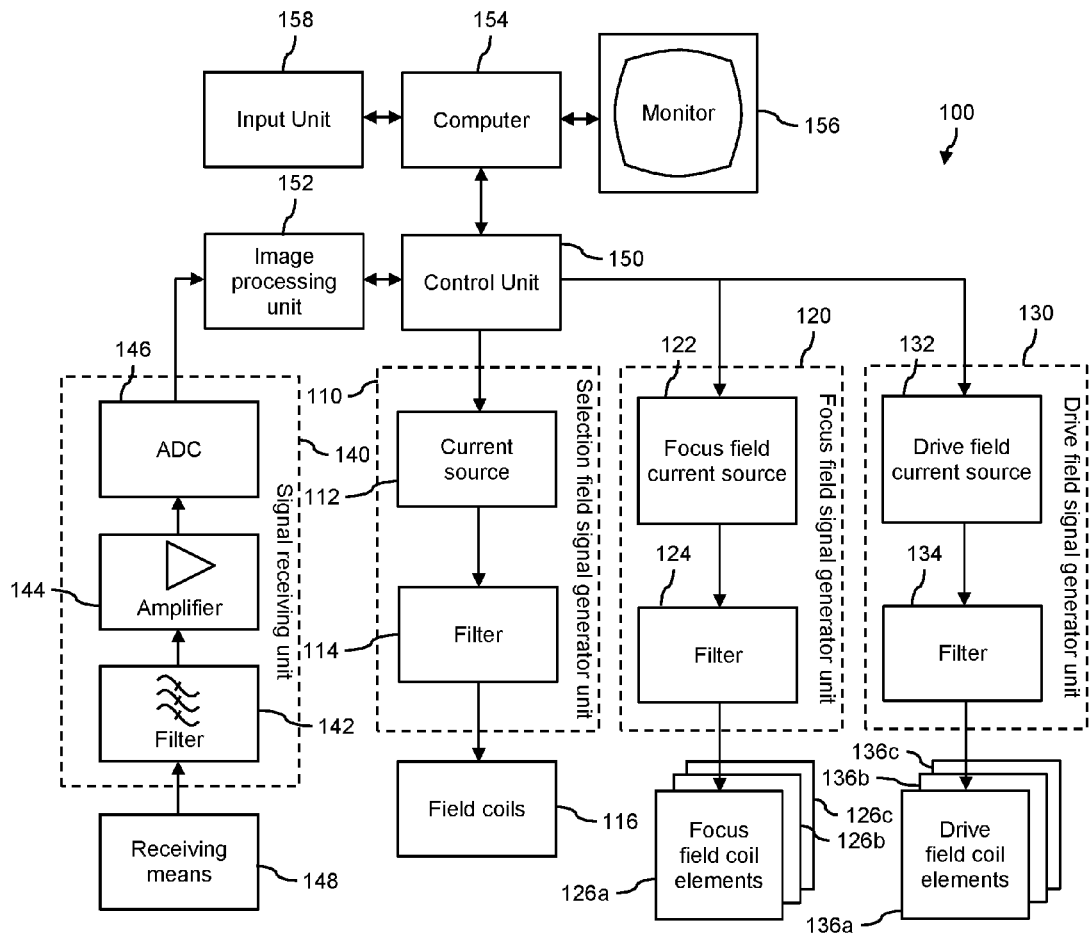
FIG. 4 shows a block diagram of an MPI apparatus according to the present invention.

FIG. 4 shows a general block diagram of an MPI apparatus 100 according to the present invention. The general principles of magnetic particle imaging explained above are valid and applicable to this embodiment as well, unless otherwise specified.

The embodiment of the apparatus 100 shown in FIG. 4 comprises various sets of coils for generating the desired magnetic fields. First, the coils and their functions in MPI shall be explained.

For generating the magnetic selection field explained above, selection means are provided comprising a set of selection field coils 116, preferably comprising at least one pair of coil elements. The selection means further comprises a selection field signal generator unit 110. Preferably, a separate generator subunit is provided for each coil element (or each pair of coil elements) of the set 116 of selection field coils. Said selection field signal generator unit 110 comprises a controllable selection field current source 112 (generally including an amplifier) and a filter unit 114 which provide the respective section field coil element with the selection field current to individually set the gradient strength of the selection field. However, since the selection field is generally static, the filter unit 114 can also be omitted. Preferably, a constant current is provided. If the selection field coil elements are arranged as opposite coils, e.g. on opposite sides of the field of view, the selection field currents of the opposite coils are preferably oppositely oriented.

The selection field signal generator unit 110 can be controlled by a control unit 150, which preferably controls the selection field current generation 110 such that the sum of the field strength and the sum of the gradient strength of all spatial fractions of the selection field is maintained at a predefined level. For this purpose the control unit 150 can also be provided with control instructions by a user according to the desired application of the MPI apparatus, which, however, is preferably omitted according to the present invention.

For the generation of a magnetic focus field the apparatus 100 further comprises focus means comprising a set of focus field coils, preferably comprising three pairs 126*a*, 126*b*, 126*c* of oppositely arranged focus field coil elements. Said magnetic focus field is generally used for changing the position in space of the first and second sub-zones. The focus field coils are controlled by a focus field signal generator unit 120, preferably comprising a separate focus field signal generation subunit for each coil element (or at least each pair of coil elements) of said set of focus field coils. Said focus field signal generator unit 120 comprises a focus field current source 122 (preferably comprising a current amplifier) and a filter unit 124 for providing a focus field current to the respective coil of said subset of coils 126*a*, 126*b*, 126*c* which shall be used for generating the magnetic focus field. The focus field current unit 120 is also controlled by the control unit 150. With the present invention, the filter unit 124 may also be omitted.

For generating the magnetic drive field the apparatus 100 further comprises drive means comprising a subset of drive field coils, preferably comprising three pairs 136*a*, 136*b*, 136*c* of oppositely arranged drive field coil elements. The drive field coils are controlled by a drive field signal generator unit 130, preferably comprising a separate drive field signal generation subunit for each coil element (or at least each pair of coil elements) of said set of drive field coils. Said drive field signal generator unit 130 comprises a drive field current source 132 (preferably including a current amplifier) and a filter unit 134 (which may also be omitted with the present invention) for providing a drive field current to the respective drive field coil. The drive field current source 132 is adapted for generating a time-dependent current and is also controlled by the control unit 150.

It should be noted that in the embodiment of the apparatus 10 shown in FIG. 1 identical coils are preferably used for generating the magnetic drive field and the magnetic focus field.

For signal detection receiving means 148, in particular a receiving coil, and a signal receiving unit 140, which receives signals detected by said receiving means 148, are provided. Preferably, three receiving coils 148 and three receiving units 140—one per receiving coil—are provided in practice, but more than three receiving coils and receiving units can be also used, in which case the acquired detection signals are not 3-dimensional but K-dimensional, with K being the number of receiving coils.

Said signal receiving unit 140 comprises a filter unit 142 for filtering the received detection signals. The aim of this filtering is to separate measured values, which are caused by the magnetization in the examination area which is influenced by the change in position of the two part-regions (52, 54), from other, interfering signals. To this end, the filter unit 142 may be designed for example such that signals which have temporal frequencies that are smaller than the temporal frequencies with which the receiving coil 148 is operated, or smaller than twice these temporal frequencies, do not pass the filter unit 142. The signals are then transmitted via an amplifier unit 144 to an analog/digital converter 146 (ADC). The digitalized signals produced by the analog/digital converter 146 are fed to an image processing unit (also called reconstruction means) 152, which reconstructs the spatial distribution of the magnetic particles from these signals and the respective position which the first part-region 52 of the first magnetic field in the examination area assumed during receipt of the respective signal and which the image processing unit 152 obtains from the control unit 150. The reconstructed spatial distribution of the magnetic particles is finally transmitted via the control means 150 to a computer 154, which displays it on a monitor 156. Thus, an image can be displayed showing the distribution of magnetic particles in the field of view of the examination area.

Further, an input unit 158 may be provided, for example a keyboard. A user may therefore be able to set the desired direction of the highest resolution and in turn receives the respective image of the region of action on the monitor 156. If the critical direction, in which the highest resolution is needed, deviates from the direction set first by the user, the user can still vary the direction manually in order to produce a further image with an improved imaging resolution. This resolution improvement process can also be operated automatically by the control unit 150 and the computer 154. The control unit 150 in this embodiment sets the gradient field in a first direction which is automatically estimated or set as start value by the user. The direction of the gradient field is then varied stepwise until the resolution of the thereby received images, which are compared by the computer 154, is maximal, respectively not improved anymore. The most critical direction can therefore be found respectively adapted automatically in order to receive the highest possible resolution.

As explained above within an MPI scanner a selection field and a drive field are superimposed. The selection field is a magnetic gradient field with a field free point (FFP). The drive field consists of different components. In the easiest case, the drive field is generated by three magnetic coils through which oscillating currents flow. These currents have different frequencies. The resulting magnetic field oscillates such that the FFP moves along a predetermined trajectory, often along a Lissajous trajectory in three dimensional space. To achieve this movement, the currents in the drive field coils must fulfill the following relations:

$$I_x(t) = I_{x01}\cos(\omega_x t) + I_{x02}\sin(\omega_x t)$$

$$I_y(t) = I_{y01}\cos(\omega_y t) + I_{y02}\sin(\omega_y t)$$

$$I_z(t) = I_{z01}\cos(\omega_z t) + I_{z02}\sin(\omega_z t), \quad (1)$$

where the frequencies $\omega_k$ and amplitudes $I_{k01}$ and $I_{k02}$ must be chosen such that the desired Lissajous trajectory results.

The drive field coils couple. This means, for example, once a current with frequency $\omega_x$ flows in the x-coil a (unwanted) current with the same frequency can also be measured in the other two drive field coils. It is the task of the controlling to compensate for this. In practice this means that the voltages generated by the drive field current sources 132, which drive the drive field coils 136a, 136b, 136c, contain components of all three frequencies on each axis.

For instance, in an embodiment of the present invention, the drive field current source for the x-coil 136a outputs a drive field voltage $$U_x(t) = U_{xx01}\cos(\omega_x t) + U_{xx02}\sin(\omega_x t) + U_{xy01}\cos(\omega_y t) + U_{xy02}\sin(\omega_y t) + U_{xz01}\cos(\omega_z t) + U_{xz02}\sin(\omega_z t). \quad (2)$$

Similar voltages $U_y(t)$ and $U_z(t)$ are output for the other two drive field coils 136b, 136c. Thus, the drive field signal generator unit 130 is adapted to provide a time-dependent oscillating drive field current per drive field coil 136a, 136b, 136c for driving the respective drive field coil, each drive field current having an individual oscillating frequency and an individual current amplitude and being generated by a corresponding drive field voltage per drive field coil 136a, 136b, 136c. As shown in equation (2) each drive field voltage is generated by a superposition of a number of drive field voltage components including a drive field voltage component per drive field coil having an individual voltage amplitude and having the same individual oscillating frequency as the drive field current of said drive field coil. Each drive field voltage component comprises a first sub-component having the form of a cosine function and a cosine voltage amplitude and a second sub-component having the form of a sine function and a sine voltage amplitude, wherein both sub-components have the same oscillating frequency. The controlling, particularly in the control unit 150, determines all amplitudes $U_{mn0k}$ such that the desired currents as defined above in equation (1) can be measured.

Figure 5:
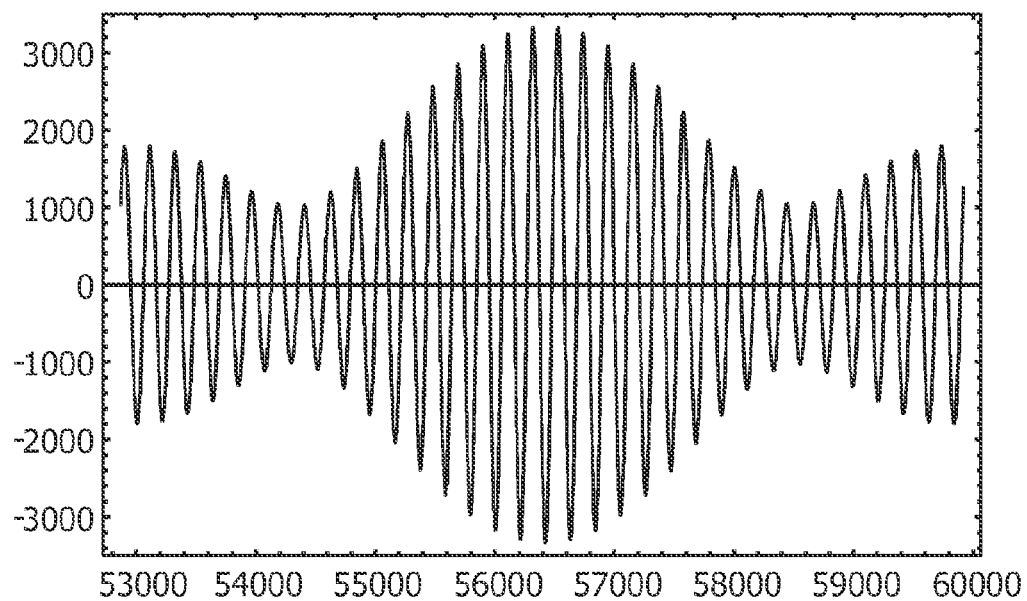
FIG. 5 shows a diagram illustrating a typical output voltage signal of a drive field current source.

Superpositions like given in equation (2) mean that the resulting signals are strong beats as illustrated in FIG. 5. The amplifiers provided in the drive field current sources 132 are limited by the maximum output power and by the maximum elongation of the voltage $U_k(t)$, where k=x, y, z. The beats reach their maxima at rare points in time only. Therefore, if the coupling is strong the maximum elongations of these beats determine the maximum amplitudes of the drive field.

This problem can be mitigated by a further embodiment of the present invention resulting in larger maximum drive field amplitudes. According to this embodiment components of higher frequency are added for the generation of voltage signals at the output of the drive field current sources like the voltage signals defined above in equation (2). For example, each term (also called drive field voltage component) of the form $U_{mn}(t) = U_{mn01}\cos(\omega_n t) + U_{mn02}\sin(\omega_n t)$ can be exchanged by a signal, which is denoted here as $\tilde{U}_{mn}(t)$. For the definition of $\tilde{U}_{mn}(t)$ angle $\alpha$ is first introduced as $$\alpha = \begin{cases} \mathrm{atan2}(U_{mn01}, U_{mn02}), & \text{if } |U_{mn02}| > |U_{mn01}| \\ \mathrm{atan2}(U_{mn02}, U_{mn01}), & \text{else,} \end{cases} \quad (3)$$

where the function a tan 2 follows the conventions of the C-programming language, i.e. the two-argument function a tan 2 is a variation of the arctangent function. For any real arguments x and y not both equal to zero, a tan 2(y, x) is the angle in radians between the positive x-axis of a plane and the point given by the coordinates (x, y) on it. The angle is positive for counter-clockwise angles (upper half-plane, y>0), and negative for clockwise angles (lower half-plane, y<0). The a tan 2 function has the advantage that, for instance compared to the a tan function, the sign of its result is automatically correct.

Now, the definition of $\tilde{U}_{mn}(t)$ is as follows:

$$\tilde{U}_{mn}(t) = \begin{cases} \dfrac{U_{mn02}}{\cos\alpha}(\sin(\beta) + \lambda_{s3}\sin(3\beta) + \lambda_{s5}\sin(5\beta) + \lambda_{s7}\sin(7\beta)), & \text{if } |U_{mn02}| > |U_{mn01}| \\ \dfrac{U_{mn01}}{\cos\alpha}(\cos(\beta) + \lambda_{c3}\cos(3\beta) + \lambda_{c5}\cos(5\beta) + \lambda_{c7}\cos(7\beta)) & \text{else.} \end{cases} \quad (4)$$

Angle β is defined as $$\beta = \begin{cases} \omega_n t + \alpha, & \text{if } |U_{mn02}| > |U_{mn01}| \\ \omega_n t - \alpha, & \text{else,} \end{cases} \quad (5)$$

and $$\lambda_{c3} = -\frac{2 \sin^2\left(\frac{\pi}{2}\kappa\right) \sin(\pi\kappa)}{3(\pi(1-\kappa) + \sin(\pi\kappa))}, \lambda_{c5} = \frac{-3 \sin(2\pi\kappa) + 2 \sin(3\pi\kappa)}{30(\pi(1-\kappa) + \sin(\pi\kappa))}, \quad (6)$$

$$\lambda_{c7} = \frac{-4 \sin(3\pi\kappa) + 3 \sin(4\pi\kappa)}{84(\pi(1-\kappa) + \sin(\pi\kappa))},$$

and $$\lambda_{s3} = \frac{2 \sin^2\left(\frac{\pi}{2}\kappa\right) \sin(\pi\kappa)}{3(\pi(1-\kappa) + \sin(\pi\kappa))}, \lambda_{s5} = \frac{-3 \sin(2\pi\kappa) + 2 \sin(3\pi\kappa)}{30(\pi(1-\kappa) + \sin(\pi\kappa))}, \quad (7)$$

$$\lambda_{s7} = \frac{4 \sin(3\pi\kappa) - 3 \sin(4\pi\kappa)}{84(\pi(1-\kappa) + \sin(\pi\kappa))},$$

wherein κ is a so-called correction parameter.

Figure 6:
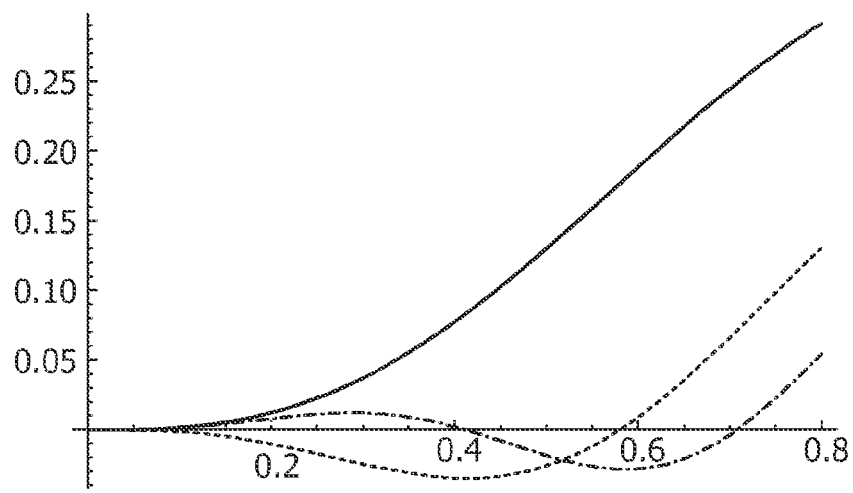
FIG. 6 shows parameters $\lambda_{s3}$, $\lambda_{s5}$ and $\lambda_{s7}$ as a function of correction parameter $\kappa$.

Generally 0≤κ<1 and κ=0 is equivalent to the correction mode turned off. Typical values of κ are in the range from 0.3 to 0.7, e.g. κ=0.4 or κ=0.55. FIG. 6 shows the values of $\lambda_{sk}$, k={3, 5, 7} as a function of κ. The value of κ can be chosen equal for all frequency contributions on all axes. Alternatively, different values of κ can be chosen for different frequency contributions and/or different axes. The lower the valued of κ is chosen, the less is the effect of the suppression of beats having a maximum beat amplitude exceeding the limit of the respective amplifier.

In the above equations, the angle α measures the relative phases of the sin- and cos-contributions to the generated signal. Functions $\tilde{U}_{mn}(t)$ follow from a Fourier-analysis of special functions, which are based on $U_{mn}(t)$. These special functions are identical to $U_{mn}(t)$ but for absolute function values which are larger than a certain threshold the special functions are set to the threshold value. Considering the mentioned Fourier series up to the seventh term and making sure that the first term, i.e. the term with the base frequency, has the same strength as in $U_{mn}(t)$, leads to equation (4). Correction parameter κ is directly related to the threshold value.

Generally, functions $\tilde{U}_{mn}(t)$ can be written as a Fourier-series as follows $$\tilde{U}_{mn}(t) = U_{mn01} \cos(\omega_n t) + U_{mn02} \sin(\omega_n t) + \sum_{k=2}^{g} (V_{mnk1} \cos(k\omega_n t) + V_{mnk2} \sin(k\omega_n t)).$$

Here g is an integer specifying the number of Fourier components to be considered. The strength of the Fourier components $V_{mnk1}$ and $V_{mnk2}$ should be chosen such that $\tilde{U}_{mn}(t)$ fulfills the desired goal in the best possible way. In particular, these components should be chosen such that the maximum elongations of the resulting drive-field generating voltages are reduced. In this sense the Fourier components $V_{mnk1}$ and $V_{mnk2}$ can be determined by the skilled person using conventional knowledge, e.g. by a mathematical analysis or a numerical computation. In the above explained particular example (equations (3) to (7)) the sin- and cos-terms are combined via the phase relationship α to single sin- and cos-contributions.

Hence, according to this embodiment the drive field signal generator unit 130 generates the drive field voltages such that each drive field voltage component comprises a superposition of two or more sub-components, wherein the first sub-component has a frequency corresponding to the oscillating frequency of the respective drive current and each further sub-component has a frequency corresponding to a different multiple of said oscillating frequency of the respective drive current. Preferably, the further sub-components have a frequency corresponding to an increasing odd multiple of said oscillating frequency of the respective drive field current.

In the above exemplary description three higher harmonics are added to the base term in equation (4). In other embodiments more or less higher harmonics may be added. Preferably, each drive field voltage component comprises a superposition of two to ten sub-components, in particular of three to five sub-components. The effect of adding more higher harmonics becomes, however, much smaller with increasing order of the harmonic. Adding two to four higher harmonics has shown to be optimum. Further, it is not required to add the higher harmonics in sequential order (e.g. as shown above the first, third and fifth harmonic), but generally any higher harmonics can be added (e.g. only the first, fifth and seventh harmonic, or only the third and fifth harmonic . . . ). In other embodiments, not only odd harmonics, but in addition (or only) even harmonics may be added to the base term.

Figure 7:
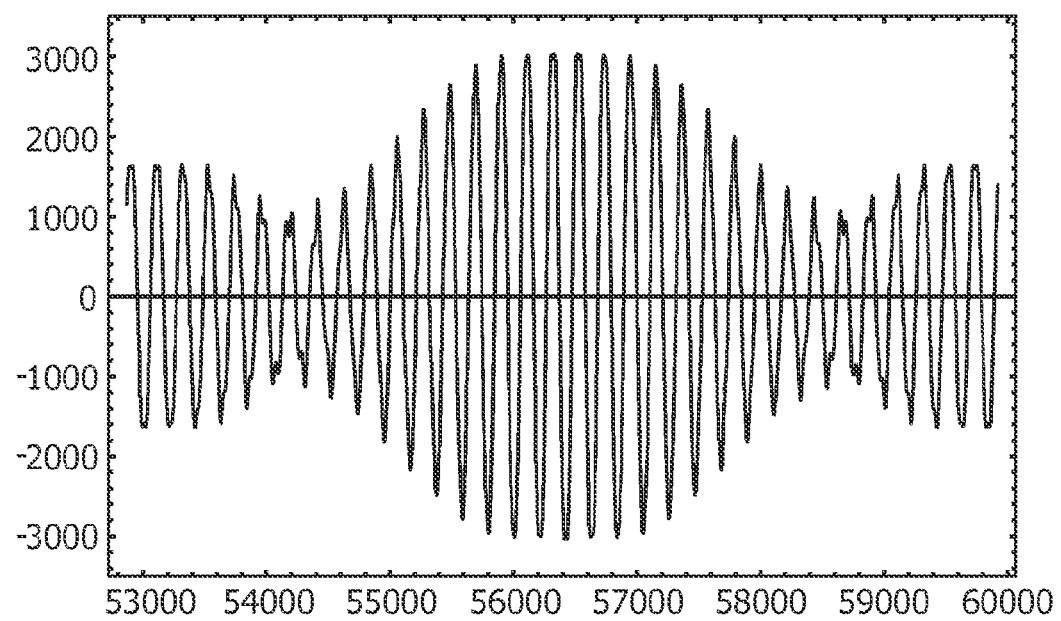
FIG. 7 shows a diagram illustrating an output voltage signal of a drive field current source after correction according to an embodiment of the present invention.

Using expressions like equation (4) in superpositions like in equation (2) results in beats in which the maximum elongation is significantly reduced as illustrated in FIG. 7. The output lines of the amplifiers are connected to low-pass filters. Therefore, the higher-frequency components in equation (4) do not enter the field generator. At the same time the components of the base frequencies in equation (4) have the same strengths as in equation (2).

In one further embodiment the additional frequency components can be turned on only temporarily. This means that the factors λ in equation (4) are set non-zero only at time intervals during which the beats have very large elongations. Switching between zero and non-zero contributions should be done at time-points at which the function values are zero. Generally, the switching can be made at predetermined time periods and/or under predetermined conditions, in particular if the amplitude of the drive field voltage used for driving the respective drive field coil exceeds a predetermined drive field voltage threshold.

In summary, MPI requires the superposition of different kinds of magnetic fields. Among these the drive field is the field which oscillates at the largest frequencies. Realizing the drive field comes with some technical challenges since the amplifiers must be able to generate signals at these frequencies with sufficient power. Moreover, the drive field coils couple, which must be compensated by a controlling mechanism. Compensation means that different signals with different frequencies must be added on each axis. This results in signals which are beats, and the maximum elongations of these beats can be the limiting factor with respect to the maximum drive field amplitude.

In cases in which the coupling between drive field coils is rather strong, the output of the amplifiers that amplify the drive signal to the drive field coils is limited by the maximum elongation of the signals at the input and output of the amplifiers. The present invention allows reducing these maximum elongations which can be used to realize larger drive field amplitudes.

Generally, signals of different frequency are added to drive the amplifiers. In embodiments of the present invention, higher components of these frequencies are used to reduce the maximum elongation of the resulting signal. Preferably, at the end a low-pass filter prevents these higher-order components from entering the field generator.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. An apparatus (100) for influencing and/or detecting magnetic particles in a field of view (28), which apparatus comprises:
   selection means comprising a selection field signal generator unit (110) and selection field elements for generating a magnetic selection field (50) having a pattern in space of its magnetic field strength such that a first sub-zone (52) having a low magnetic field strength where the magnetization of the magnetic particles is not saturated and a second sub-zone (54) having a higher magnetic field strength where the magnetization of the magnetic particles is saturated are formed in the field of view (28),
   drive means comprising a drive field signal generator unit (130) and drive field coils (136a, 136b, 136c) for changing the position in space of the two sub-zones (52, 54) in the field of view (28) by means of a magnetic drive field so that the magnetization of the magnetic particles changes locally,
   receiving means comprising at least one receiving coil for acquiring detection signals, which detection signals depend on the magnetization of the magnetic particles in the field of view (28), which magnetization is influenced by the change in the position in space of the first and second sub-zone (52, 54),
   wherein said drive field signal generator unit (130) is adapted to provide a time-dependent oscillating drive field current per drive field coil for driving the respective drive field coil, each drive field current having one or more individual oscillating frequencies and one or more individual current amplitudes and being generated by a corresponding drive field voltage per drive field coil (136a, 136b, 136c), each drive field voltage being generated by a superposition of a number of drive field voltage components including a drive field voltage component per drive field coil, wherein a drive field voltage component corresponding to a particular drive field coil comprises one or more sub-components, at least one sub-component having an individual voltage amplitude and having the same individual oscillating frequency as the respective drive field current of said particular drive field coil.

2. An apparatus (100) as claimed in claim 1, wherein said drive field signal generator unit (130) is adapted to generate said drive field voltages such that each drive field voltage component comprises a first sub-component having the form of a cosine function and a cosine voltage amplitude and a second sub-component having the form of a sine function and a sine voltage amplitude, wherein both sub-components have the same oscillating frequency.

3. An apparatus (100) as claimed in claim 2, wherein each drive field voltage is represented by $U_m(t)$ and has the form of $$U_m(t) = U_{mx01} \cos(\omega_x t) + U_{mx02} \sin(\omega_x t) + U_{my01} \cos(\omega_y t) + U_{my02} \sin(\omega_y t) + U_{mz01} \cos(\omega_z t) + U_{mz02} \sin(\omega_z t)$$

wherein m=x, y, z depending on the respective drive field coil, ω is the respective oscillating frequency and $U_{mn01}$ and $U_{mn02}$, n=x, y, z, are the respective voltage amplitudes.

4. An apparatus (100) as claimed in claim 1, wherein said drive field signal generator unit (130) is adapted to generate said drive field voltages such that at least one drive field voltage component comprises a superposition of two or more sub-components, wherein the first sub-component has a frequency corresponding to the oscillating frequency of the respective drive field current of said particular drive field coil and at least one further sub-component has a frequency corresponding to a different multiple of said oscillating frequency of said respective drive field current.

5. An apparatus (100) as claimed in claim 4, wherein said further sub-components have a frequency corresponding to an increasing odd multiple of said oscillating frequency of said respective drive field current.

6. An apparatus (100) as claimed in claim 4, wherein said each drive field voltage component comprises a superposition of two to ten sub-components.

7. An apparatus (100) as claimed in claim 4, wherein each drive field voltage is represented by $\tilde{U}_m(t)$ and has the form of $$\tilde{U}_m(t) = \tilde{U}_{mx}(t) + \tilde{U}_{my}(t) + \tilde{U}_{mz}(t),$$

wherein each component $\tilde{U}_{mn}(t)$ has the form of $$\tilde{U}_{mn}(t) = \begin{cases} \dfrac{U_{mn02}}{\cos \alpha}(\sin(\beta) + \lambda_{s3} \sin(3\beta) + \lambda_{s5} \sin(5\beta) + \lambda_{s7} \sin(7\beta)), & \text{if } |U_{mn02}| > |U_{mn01}| \\ \dfrac{U_{mn01}}{\cos \alpha}(\cos(\beta) + \lambda_{c3} \cos(3\beta) + \lambda_{c5} \cos(5\beta) + \lambda_{c7} \cos(7\beta)) & \text{else.} \end{cases}$$

wherein

-continued $$\alpha = \begin{cases} \text{atan2}(U_{mn01}, U_{mn02}), & \text{if } |U_{mn02}| > |U_{mn01}| \\ \text{atan2}(U_{mn02}, U_{mn01}), & \text{else,} \end{cases}$$

$$\beta = \begin{cases} \omega_n t + \alpha, & \text{if } |U_{mn02}| > |U_{mn01}| \\ \omega_n t - \alpha, & \text{else,} \end{cases}$$

$$\lambda_{c3} = -\frac{2\sin^2\left(\frac{\pi}{2}\kappa\right)\sin(\pi\kappa)}{3(\pi(1-\kappa)+\sin(\pi\kappa))}, \lambda_{c5} = \frac{-3\sin(2\pi\kappa)+2\sin(3\pi\kappa)}{30(\pi(1-\kappa)+\sin(\pi\kappa))}, \lambda_{c7} = \frac{-4\sin(3\pi\kappa)+3\sin(4\pi\kappa)}{84(\pi(1-\kappa)+\sin(\pi\kappa))},$$

and $$\lambda_{s3} = \frac{2\sin^2\left(\frac{\pi}{2}\kappa\right)\sin(\pi\kappa)}{3(\pi(1-\kappa)+\sin(\pi\kappa))}, \lambda_{s5} = \frac{-3\sin(2\pi\kappa)+2\sin(3\pi\kappa)}{30(\pi(1-\kappa)+\sin(\pi\kappa))}, \lambda_{s7} = \frac{4\sin(3\pi\kappa)-3\sin(4\pi\kappa)}{84(\pi(1-\kappa)+\sin(\pi\kappa))},$$

wherein κ is a correction parameter.

8. An apparatus (100) as claimed in claim 7,
wherein said correction parameter κ has an identical predetermined value for all sub-components or different values for different sub-components and/or different frequencies and/or axes of said sub-components and wherein said value is in the range from 0 to 1.

9. An apparatus (100) as claimed in claim 4,
wherein said drive field signal generator unit (130) further comprises a drive field generator control unit (138) for controlling the generation of said drive field voltages such that one or more, further sub-components having a frequency corresponding to a different multiple of said oscillating frequency of said respective drive field current are switchably added to the first sub-component only when the amplitude of the drive field voltage exceeds a predetermined drive field voltage threshold.

10. An apparatus (100) as claimed in claim 9,
wherein said drive field generator control unit (138) is adapted for switching the addition of one or more further sub-components at time points at which the respective sub-component has a function value of zero.

11. An apparatus (100) as claimed in claim 4,
wherein said drive field signal generator unit (130) comprises an amplifier (132) for amplifying said drive field voltages and a filter (134) for filtering out the further sub-components after amplification.

12. A method for influencing and/or detecting magnetic particles in a field of view (28), which method comprises the steps of:
generating a magnetic selection field (50) having a pattern in space of its magnetic field strength such that a first sub-zone (52) having a low magnetic field strength where the magnetization of the magnetic particles is not saturated and a second sub-zone (54) having a higher magnetic field strength where the magnetization of the magnetic particles is saturated are formed in the field of view (28),
changing the position in space of the two sub-zones (52, 54) in the field of view (28) by means of a magnetic drive field by drive field coils (136a, 136b, 136c) so that the magnetization of the magnetic particles changes locally,
providing a time-dependent oscillating drive field current per drive field coil for driving the respective drive field coil, each drive field current having one or more individual oscillating frequencies and one or more individual current amplitudes and being generated by a corresponding drive field voltage per drive field coil (136a, 136b, 136c), each drive field voltage being generated by a superposition of a number of drive field voltage components including a drive field voltage component per drive field coil, wherein a drive field voltage component corresponding to a particular drive field coil comprises one or more sub-components, at least one sub-component having an individual voltage amplitude and having the same individual oscillating frequency as the respective drive field current of said particular drive field coil, and
acquiring detection signals, which detection signals depend on the magnetization of the magnetic particles in the field of view (28), which magnetization is influenced by the change in the position in space of the first and second sub-zone (52, 54).

13. A Computer program product, comprising a non-transient computer readable storage device having encoded thereon program code means for influencing and/or detecting magnetic particles in a field of view (28) by causing a computer to control an apparatus to perform the steps of
generating a magnetic selection field (50) having a pattern in space of its magnetic field strength such that a first sub-zone (52) having a low magnetic field strength where the magnetization of the magnetic particles is not saturated and a second sub-zone (54) having a higher magnetic field strength where the magnetization of the magnetic particles is saturated are formed in the field of view (28),
changing the position in space of the two sub-zones (52, 54) in the field of view (28) by means of a magnetic drive field by drive field coils (136a, 136b, 136c) so that the magnetization of the magnetic particles changes locally,
providing a time-dependent oscillating drive field current per drive field coil for driving the respective drive field coil, each drive field current having one or more individual oscillating frequencies and one or more individual current amplitudes and being generated by a corresponding drive field voltage per drive field coil (136a, 136b, 136c), each drive field voltage being generated by a superposition of a number of drive field voltage components including a drive field voltage component per drive field coil, wherein a drive field voltage component corresponding to a particular drive field coil comprises one or more sub-components, at least one sub-component having an individual voltage amplitude and having the same individual oscillating frequency as the respective drive field current of said particular drive field coil, and acquiring detection signals, which detection signals depend on the magnetization of the magnetic particles in the field of view (28), which magnetization is influenced by the change in the position in space of the first and second sub-zone (52, 54).

\* \* \* \* \*